US008150055B2

(12) United States Patent
Sakamoto et al.

(10) Patent No.: US 8,150,055 B2
(45) Date of Patent: Apr. 3, 2012

(54) ACTIVE NOISE CONTROL SYSTEM AND ACTIVE VIBRATION CONTROL SYSTEM

(75) Inventors: Kosuke Sakamoto, Utsunomiya (JP); Toshio Inoue, Tochigi-ken (JP); Akira Takahashi, Tochigi-ken (JP); Yasunori Kobayashi, Utsunomiya (JP)

(73) Assignee: Honda Motor Co., Ltd., Tokyo (JP)

( * ) Notice: Subject to any disclaimer, the term of this patent is extended or adjusted under 35 U.S.C. 154(b) by 1376 days.

(21) Appl. No.: 11/723,435

(22) Filed: Mar. 20, 2007

(65) Prior Publication Data

US 2007/0233478 A1 Oct. 4, 2007

(30) Foreign Application Priority Data

Mar. 31, 2006 (JP) .................................. 2006-99189

(51) Int. Cl.
*G10K 11/16* (2006.01)
*A61F 11/06* (2006.01)

(52) U.S. Cl. ..................... 381/71.4; 381/71.1; 381/71.2; 381/71.8; 381/71.11

(58) Field of Classification Search ................. 381/71.1, 381/71.4, 71.8, 71.11, 86
See application file for complete search history.

(56) References Cited

U.S. PATENT DOCUMENTS 7,352,869 B2 4/2008 Inoue et al.
2004/0247137 A1 * 12/2004 Inoue et al. ................. 381/71.4

FOREIGN PATENT DOCUMENTS

JP 03-204354 9/1991
JP 2827374 B2 9/1998
JP 2004361721 A 12/2004

* cited by examiner

*Primary Examiner* — Devona Faulk
*Assistant Examiner* — George Monikang
(74) *Attorney, Agent, or Firm* — Arent Fox, LLP

(57) ABSTRACT

An active noise control system includes a filter coefficient updating unit including an imaginary term estimator. The imaginary term estimator estimates an imaginary term Ie from a real term Re of an error signal e supplied from a microphone. The filter coefficient updating unit updates a filter coefficient W of an adaptive filter based on the imaginary term Ie, the real term Re, and a corrective signal supplied from a reference signal corrector. The filter coefficient updating unit updates the filter coefficient W successively in respective sampling periods.

21 Claims, 10 Drawing Sheets

ACTIVE NOISE CONTROL SYSTEM AND ACTIVE VIBRATION CONTROL SYSTEM

CROSS-REFERENCE TO RELATED APPLICATION

This application claims the priority of Japanese Application No. 2006-99189, filed Mar. 31, 2006 the entire specification, claims and drawings of which are incorporated herewith by reference.

BACKGROUND OF THE INVENTION

1. Field of the Invention

The present invention relates to an active noise control system for reducing second noise that is generated in a vehicle based on first noise generated by a noise source such as an engine or the like on the vehicle, with third noise that is generated as a noise for canceling out the second noise, and an active vibration control system for reducing second vibration that is generated in a vehicle based on first vibration generated by a vibration source such as an engine or the like on the vehicle, with third vibration that is generated as vibration for canceling out the second vibration.

2. Description of the Related Art

There has recently been proposed an active noise control system for detecting noise in the passenger compartment of a vehicle, which is caused by noise or vibration generated by a noise source such as an engine or the like on the vehicle, with a microphone disposed in the vicinity of the ears of a passenger in the passenger compartment, and generating a control signal based on the detected noise (see Japanese patent No. 2827374).

In the active noise control system, the control signal is output to speakers disposed in the passenger compartment, and the speakers radiate canceling noise based on the control signal into the passenger compartment for canceling out the noise at the ears of the passenger with the canceling noise.

The noise (vibration) generated by the engine as the noise (vibration) source represents periodic noise (vibration) caused by engine sounds and vibrational forces generated by the rotation of the engine output shaft. Therefore, the noise produced in the passenger compartment due to the noise (vibration) generated by the noise (vibration) source also represents periodic noise (vibration). Since the noise in the passenger compartment comprises a real component and an imaginary component, ideally, an error signal output from an ideal microphone comprises a real component (real term) and an imaginary component (imaginary term).

An actual microphone, however, is capable of detecting a real term of the noise only, and an error signal output from the actual microphone comprises a real term only. Therefore, the active noise control system which employs the actual microphone generates a control signal based on the detected real term of the noise and a reference signal.

Specifically, an ECU of the active noise control system ignores any imaginary term of the error signal, and updates the filter coefficients of an adaptive filer based on the real term of the error signal and the reference signal. The adaptive filter generates a control signal based on the reference signal using the updated filter coefficient. The canceling noise radiated from the speakers based on the control signal represents sounds depending on the real part of the error signal.

As described above, since the noise in the passenger compartment is periodic noise having certain frequencies which is made up of a real term and an imaginary term, the noise in the passenger compartment cannot reliably be reduced in a short period of time even though the canceling noise depending on the real term is radiated into the passenger compartment.

Furthermore, because the vibration from the engine as the vibration source on the vehicle is periodic vibration, the vibration produced in the passenger compartment by the periodic vibration cannot reliably be reduced in a short period of time unless the imaginary term of the vibration is taken into account.

SUMMARY OF THE INVENTION

It is an object of the present invention to provide an active noise control system for reliably reducing noise in the vicinity of the ears of passengers in a passenger compartment within a short period of time, and an active vibration control system for reliably reducing vibration in a passenger compartment.

According to the present invention, an active noise control system comprises an adaptive filter for being supplied with a reference signal that is correlated to first noise generated by a noise source on a vehicle, and generating a control signal based on the reference signal, noise output means for outputting third noise based on the control signal in order to cancel out second noise generated in the vehicle based on the first noise, noise detecting means for generating an error signal based on canceling error noise between the second noise and the third noise, reference signal correcting means for correcting the reference signal based on sound transfer characteristics from the noise output means to the noise detecting means, and outputting the corrected reference signal as a corrective signal, and filter coefficient updating means, having an imaginary term estimator for estimating an imaginary term of the error signal based on the error signal which comprises a real term, for updating a filter coefficient of the adaptive filter in order to minimize the error signal, based on the imaginary term estimated by the imaginary term estimator, the real term, and the corrective signal.

With the above arrangement, the imaginary term estimator estimates the imaginary term of the error signal, and the filter coefficient updating means updates the filter coefficient based on the real term and the imaginary term of the error signal and the corrective signal. Consequently, the updating quantity for the filter coefficient is greater than the conventional system wherein the filter coefficient is updated using only the real term and the corrective signal while ignoring the imaginary term. As a result, the noise in the vicinity of the ears of passengers in the passenger compartment of the vehicle can reliably be reduced within a short period of time.

The imaginary term estimator may have a real term differentiator for calculating a time differential value of the real term, and estimate the imaginary term based on the time differential value calculated by the real term differentiator. Alternatively, the imaginary term estimator may have a real term integrator for calculating a time integral value of the real term, and estimate the imaginary term based on the time integral value calculated by the real term integrator. Since the time differential value or the time integral value can be calculated and the imaginary term can be estimated in a predetermined sampling period, the noise in the passenger compartment can efficiently be reduced.

The imaginary term estimator may further have a first filter for dividing the time differential value calculated by the real term differentiator by an angular frequency corresponding to the frequency of the error signal and multiplying the time differential value by −1, or for multiplying, by the angular frequency, the time integral value calculated by the real term integrator. If the error signal is a periodic signal and the frequency of the error signal is known, then the component of the angular frequency generated when the time differential value or the time integral value is calculated can be canceled. Therefore, the imaginary term can be estimated with accuracy.

The imaginary term estimator may further have a first filter having either characteristics represented by the reciprocal, multiplied by −1, of an angular frequency corresponding to the frequency of the error signal for passing therethrough the time differential value calculated by the real term differentiator, or characteristics represented by the angular frequency for passing therethrough the time integral value calculated by the real term integrator. If the error signal is a periodic signal and the frequency of the error signal is unknown, then the time differential value or the time integral value is passed through the first filter having the characteristics represented by the reciprocal, multiplied by −1, of the angular frequency or the characteristics represented by the angular frequency as the frequency response characteristics, thereby canceling the component of the angular frequency generated when the time differential value or the time integral value is calculated. Therefore, the imaginary term can also be estimated with accuracy.

The imaginary term estimator may have a second filter for dividing the corrective signal by an angular frequency corresponding to the frequency of the error signal and multiplying the corrective signal by −1.

When the filter coefficient updating means updates the filter coefficient, the updating quantity for the filter coefficient includes the error signal, the reference signal, and the corrective signal (the product of the sound transfer characteristics and the reference signal). Therefore, with respect to the updating quantity, dividing the error signal by the angular frequency is synonymous with dividing the reference signal by the angular frequency or dividing the corrective signal by the angular frequency. Consequently, dividing the corrective signal by the angular frequency is synonymous with dividing the time differential value by the angular frequency.

The imaginary term estimator may have a second filter having characteristics represented by the reciprocal, multiplied by −1, of an angular frequency corresponding to the frequency of the error signal, for passing the corrective signal therethrough.

The imaginary term estimator may have a third filter for dividing the reference signal by an angular frequency corresponding to the frequency of the error signal and multiplying the reference signal by −1, and a reference signal corrector for correcting the divided and multiplied reference signal based on the sound transfer characteristics. For the reasons described above, dividing the reference signal by the angular frequency is synonymous with dividing the time differential value by the angular frequency.

The imaginary term estimator may have a third filter having characteristics represented by the reciprocal, multiplied by −1, of an angular frequency corresponding to the frequency of the error signal, for passing the corrective signal therethrough, and a reference signal corrector for correcting the reference signal having passed through the third filter based on the sound transfer characteristics.

When the control signal and the corrective signal are generated, the third noise is output, the error signal is detected, and the filter coefficient is updated successively in each given sampling period, the real term differentiator may calculate the time differential value by dividing, by the sampling period, the difference between the real term of the error signal that is input in a present sampling cycle and the real term of the error signal that is input in a preceding sampling cycle. In this manner, the imaginary term can easily be calculated.

If the sampling period is a fixed sampling period, the imaginary term estimator may estimate the imaginary term by dividing the difference by the fixed sampling period and the frequency of the error signal and multiplying the difference by −1. If the sampling period is a variable sampling period, the imaginary term estimator may estimate the imaginary term by multiplying the difference by a number representing the reciprocal of the product of the variable sampling period and the frequency of the error signal and by −1. In this manner, it is possible to estimate the imaginary term regardless of the fixed sampling period process or the variable sampling period process.

If the sampling period is a fixed sampling period, the imaginary term estimator may estimate the imaginary term by dividing the difference by the fixed sampling period and passing the divided difference through a first filter having characteristics represented by the reciprocal, multiplied by −1, of an angular frequency corresponding to the frequency of the error signal. If the sampling period is a variable sampling period, the imaginary term estimator may estimate the imaginary term by dividing the difference by the variable sampling period and passing the divided difference through a first filter having characteristics represented by the reciprocal, multiplied by −1, of an angular frequency corresponding to the frequency of the error signal. In this manner, it is also possible to estimate the imaginary term regardless of the fixed sampling period process or the variable sampling period process.

When the control signal and the corrective signal are generated, the third noise is output, the error signal is detected, and the filter coefficient is updated successively in each given sampling period, the real term integrator may calculate the time integral value by multiplying, by the sampling period, the sum of the real term of the error signal that is input in a present sampling cycle and the real term of the error signal that is input in a preceding sampling cycle. In this manner, the imaginary term can easily be calculated.

If the sampling period is a fixed sampling period, the imaginary term estimator may estimate the imaginary term by multiplying the sum by the fixed sampling period and the frequency of the error signal. If the sampling period is a variable sampling period, the imaginary term estimator may estimate the imaginary term by dividing the sum by a number representing the reciprocal of the product of the variable sampling period and the frequency of the error signal. In this manner, it is possible to estimate the imaginary term regardless of the fixed sampling period process or the variable sampling period process.

If the sampling period is a fixed sampling period, the imaginary term estimator may estimate the imaginary term by multiplying the sum by the fixed sampling period and passing the multiplied sum through a first filter having characteristics represented by an angular frequency corresponding to the frequency of the error signal. If the sampling period is a variable sampling period, the imaginary term estimator may estimate the imaginary term by multiplying the sum by the variable sampling period and passing the multiplied sum through a first filter having characteristics represented by an angular frequency corresponding to the frequency of the error signal. In this manner, it is also possible to estimate the imaginary term regardless of the fixed sampling period process or the variable sampling period process.

The noise source comprises an engine on the vehicle. The second noise comprises noise produced in a passenger compartment of the vehicle. The noise output means comprises a speaker disposed in the passenger compartment. The noise detecting means comprises a microphone disposed in the passenger compartment. With these arrangements, the noise produced in the passenger compartment by the noise generated by the engine can reliably be reduced in a short period of time.

According to the present invention, an active vibration control system comprises an adaptive filter for being supplied with a reference signal that is correlated to first vibration generated by a vibration source on a vehicle, and generating a control signal based on the reference signal, vibration output means for outputting third vibration based on the control signal in order to cancel out second vibration generated in the vehicle based on the first vibration, vibration detecting means for generating an error signal based on canceling error vibration between the second vibration and the third vibration, reference signal correcting means for correcting the reference signal based on vibration transfer characteristics from the vibration output means to the vibration detecting means, and outputting the corrected reference signal as a corrective signal, and filter coefficient updating means, having an imaginary term estimator for estimating an imaginary term of the error signal based on the error signal which comprises a real term, for updating a filter coefficient of the adaptive filter in order to minimize the error signal, based on the imaginary term estimated by the imaginary term estimator, the real term, and the corrective signal.

With the above arrangement, the imaginary term estimator estimates the imaginary term of the error signal, and the filter coefficient updating means updates the filter coefficient based on the real term and the imaginary term of the error signal and the corrective signal. Consequently, the updating quantity for the filter coefficient is increased. As a result, the vibration in the vehicle can reliably be reduced within a short period of time.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
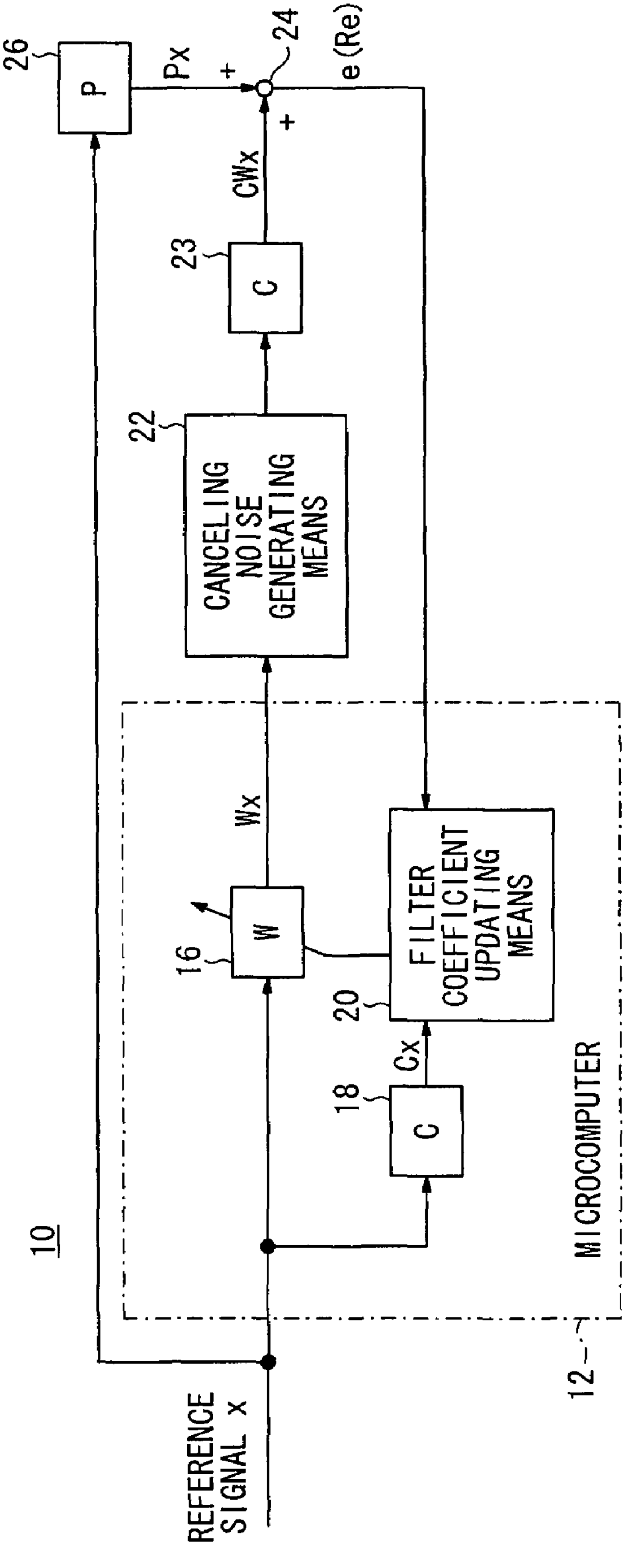
FIG. 1 is a block diagram of an active noise control system (ANC) as a basis of the present invention.

FIG. 1 shows in block form an active noise control system (ANC) 10 as a basis for the present invention.

As shown in FIG. 1, the active noise control system 10, which is incorporated in a vehicle, not shown, basically comprises a microcomputer 12 serving as an ECU, a canceling noise generating means (noise outputting means) 22 such as door speakers and rear speakers disposed in the passenger compartment of the vehicle, and a microphone (noise detecting means) 24 disposed in the vicinity of the ears of each passenger in the passenger compartment, e.g., in the vicinity of the head rest of each passenger seat in the passenger compartment.

The microcomputer 12 has, as its functional components, an adaptive filter 16 such as an adaptive notch filter, an FIR filter, or the like, a reference signal correcting means 18, and a filter coefficient updating means 20.

The adaptive filter 16 is supplied with a reference signal x (e.g. an engine pulse produced by a Hall device or the like per revolution of the output shaft of the engine on the vehicle) that is correlated to noise (first noise) (e.g., periodic noise caused by engine sounds and vibrational forces generated by the rotation of the engine output shaft) generated by a noise source such as the engine. The adaptive filter 16 generates a control signal (=W×x) based on the reference signal x and a filter coefficient W thereof.

When the reference signal x is output to an unknown plant 26 which may be the vehicle body or the like, noise (second noise) represented by P×x is generated in the passenger compartment based on the reference signal x and a transfer function P of the plant 26. At this time, the canceling noise generating means 22 radiates canceling noise (third noise) based on the control signal from the microcomputer 12 into the passenger compartment.

The microphone 24 detects canceling error noise between the noise (=P×x) in the vicinity of the ears of the passengers in the passenger compartment and the canceling noise {=C×W×x, C: the sound transfer characteristics in a transmission path (sound field) 23 from the canceling noise generating means 22 to the microphone 24}, and outputs an error signal e based on the canceling error noise to the filter coefficient updating means 20.

The reference signal correcting means 18 multiplies the reference signal x by the sound transfer characteristics C (or a model with the sound transfer characteristics) to produce a corrective signal (=C×x), and outputs the corrective signal to the filter coefficient updating means 20.

The filter coefficient updating means 20, which comprises a least mean squares (LMS) algorithm processor, performs an adaptive calculation process for a filter coefficient W, i.e., a calculation process for calculating a filter coefficient W to minimize the error signal e according to the LMS method, based on the corrective signal from the reference signal correcting means 18 and the error signal e from the microphone 24, and updates the filter coefficient W of the adaptive filter 16 based on the calculated filter coefficient W.

The active noise control system 10 generates the control signal and the corrective signal, outputs the canceling noise and the error signal e, and updates the filter coefficient W successively in respective sampling periods.

Conditions (the filter coefficient W and its updating quantity) for minimizing the error signal e, i.e., for canceling out the noise in the position of the microphone 24, and a task to be achieved by the active noise control system 10 will be described below with reference to FIGS. 1, 2A, and 2B.

As shown in FIG. 1, the error signal e is expressed by the following equation (1):

$$e=P\cdot x+C\cdot W\cdot x \tag{1}$$

As described above, since the noise generated by the noise source such as the engine is periodic noise, i.e., noise having certain frequencies, the reference signal x and the error signal e including the reference signal x can be expressed by a complex number comprising a real term (real component) Re and an imaginary term (imaginary component) Ie, according to the equation (2):

$$e=Re+iIe \tag{2}$$

where i represents an imaginary unit.

Inasmuch as the microphone 24 detects only the real term of the canceling error noise, the error signal e that is actually output from the microphone 24 comprises only the real term Re. Therefore, the canceling noise generating means 22 outputs canceling noise in order to minimize the real term Re of the error signal e, as indicated by the following equation (3):

$$|e|^2=Re^2+Ie^2\rightarrow|e|^2=Re^2\rightarrow\text{minimum} \tag{3}$$

The filter coefficient W, the reference signal x, the transfer function P of the plant 26, and the sound transfer characteristics C are expressed by complex numbers according to the equations (4) through (7) shown below, and the filter coefficient Wn in a present sampling cycle is expressed according to the equation (8) shown below. In the equations (4) through (8), Rw, Rx, Rp, Rc, and Rwn represent the real terms of W, x, P, C, and Wn, respectively, and Iw, Ix, Ip, Ic, and Iwn represent the imaginary terms of W, x, P, C, and Wn, respectively.

$$W=Rw+iIw \tag{4}$$

$$x=Rx+iIx \tag{5}$$

$$P=Rp+iIp \tag{6}$$

$$C=Rc+iIc \tag{7}$$

$$Wn=Rwn+iIwn \tag{8}$$

From the equations (1), (2) and (4) through (7), the error signal e, the real term Re, and the imaginary term Ie are expressed according to the following equations (9) through (11):

$$\begin{aligned} e &= (P+C\cdot W)x \\ &= \{(Rp+Rc\cdot Rw-Ic\cdot Iw)Rx - \\ &\quad (Ip+Rc\cdot Iw+Ic\cdot Rw)Ix\} + \\ &\quad i\{(Rp+Rc\cdot Rw-Ic\cdot Iw)Ix + \\ &\quad (Ip+Rc\cdot Iw+Ic\cdot Rw)Rx \end{aligned} \tag{9}$$

$$\begin{aligned} \mathrm{Re} = &(Rp+Rc\cdot Rw+Ic\cdot Iw)Rx - \\ &(Ip+Rc\cdot Iw+Ic\cdot Rw)Ix \end{aligned} \tag{10}$$

-continued $$\begin{aligned} Ie = &(Rp+Rc\cdot Rw-Ic\cdot Rw)Ix + \\ &(Ip+Rc\cdot Iw+Ic\cdot Rw)Rx \end{aligned} \tag{11}$$

As indicated by the equation (3), since $|e|^2$ is the sum of $Re^2$ and $Ie^2$, $|e|^2$ is a quadratic function of Rw and Iw according to the equations (10) and (11).

If a value (optimum value) of the filter coefficient W for minimizing the error signal e is represented by $W_{OPT}$, then the filter coefficient W is expressed according to the following equation (12):

$$W=W_{OPT}=-C^{-1}P\rightarrow\frac{\partial|e|^2}{\partial W}=0 \tag{12}$$

The relationship between the filter coefficient W and $C^{-1}\cdot P$ is expressed according to the following equations (13) and (14):

$$W>C^{-1}P\rightarrow\frac{\partial|e|^2}{\partial W}>0 \tag{13}$$

$$W<C^{-1}P\rightarrow\frac{\partial|e|^2}{\partial W}<0 \tag{14}$$

As the filter coefficient W is successively updated according to the equation (15) shown below, the error signal e approaches its minimum value according to the LMS method. In the equation (15), the suffix n+1 indicates a next sampling cycle and α a predetermined number.

$$W_{n+1}=W_n-\alpha\frac{\partial|e|^2}{\partial W} \tag{15}$$

Actually, the equation (15) is divided into the real term and the imaginary term, which are calculated according to the LMS method, as indicated by the following equations (16) through (19):

$$R_{W_{n+1}}=R_{W_n}-\alpha\frac{\partial|e|^2}{\partial R_W} \tag{16}$$

$$I_{W_{n+1}}=I_{W_n}-\alpha\frac{\partial|e|^2}{\partial I_W} \tag{17}$$

$$\begin{aligned} \frac{\partial|e|^2}{\partial R_W} &= 2R_e\cdot\frac{\partial R_e}{\partial R_W} \\ &= 2R_e\cdot(R_C R_x - I_C I_x) \end{aligned} \tag{18}$$

$$\begin{aligned} \frac{\partial|e|^2}{\partial I_W} &= 2R_e\cdot\frac{\partial R_e}{\partial I_W} \\ &= 2R_e\cdot(-I_C R_x - R_C I_x) \end{aligned} \tag{19}$$

As a consequence, the equations for updating the filter coefficient W are given as the equations (20) and (21) shown below. In the equations (20) and (21), μ represents a step size parameter with respect to the updating quantity for the filter coefficient W. The first term on the right side of each of the equations (20) and (21) represents a real term or an imaginary term of the filter coefficient in the present sampling cycle, and the second term on the right side thereof represents an updating quantity for (the real term and the imaginary term of) the filter coefficient W.

$$Rw_{n+1}=Rwn-\mu\cdot Re\cdot(Rc\cdot Rx-Ic\cdot Ix) \quad (20)$$

$$IW_{n+1}=Iwn+\mu\cdot Re\cdot(Ic-Rx+Rc\cdot Ix) \quad (21)$$

Figure 2A:
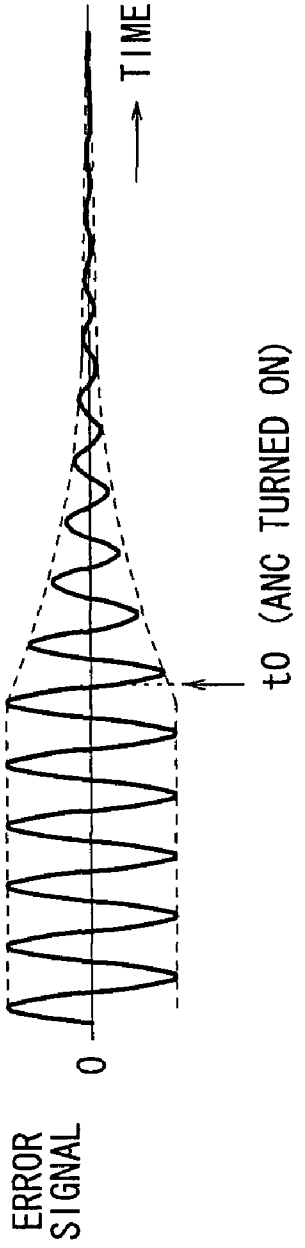
FIG. 2A is a diagram showing time-dependent changes of an error signal which occur when the active noise control system shown in FIG. 1 operates.
Figure 2B:
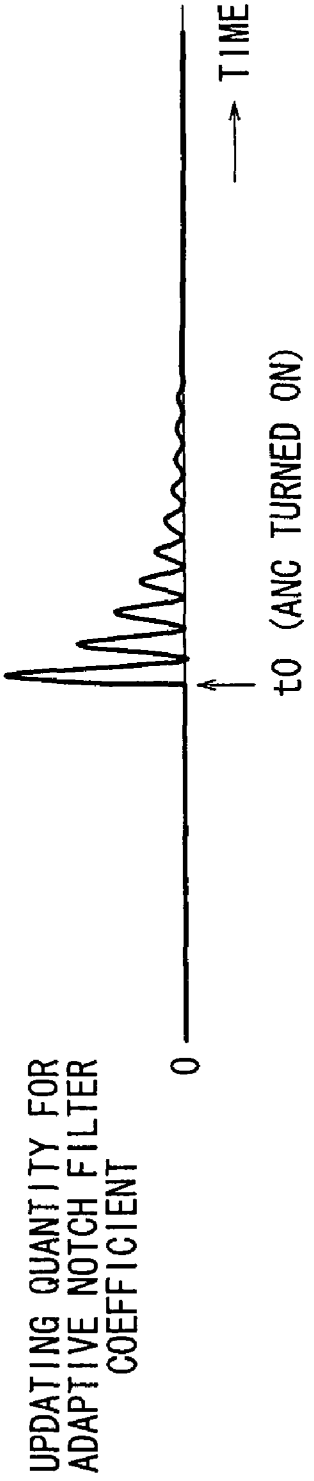
FIG. 2B is a diagram showing time-dependent changes of an updating quantity for a filter coefficient which occur when the active noise control system shown in FIG. 1 operates.

FIG. 2A shows time-dependent changes of the error signal e, and FIG. 2B shows time-dependent changes of the updating quantity {represented by the second term on the right side of each of the equations (20) and (21)} for the filter coefficient W. In FIGS. 2A and 2B, the active noise control system 10 changes from an off-state to an on-state at time t0.

As indicated by the equations (20) and (21), since the updating quantity for the filter coefficient W is proportional to the real term Re of the error signal e, the updating quantity for the filter coefficient W is larger (see FIG. 2B) at times when the level of the error signal e is higher (see FIG. 2A), and is smaller at times when the level of the error signal e is lower. In other words, the updating quantity for the filter coefficient W changes in synchronism with the time-dependent change in the level of the error signal e. It takes a long period of time until the level of the error signal e converges to a zero level, i.e., a level where the noise in the passenger compartment is canceled out by the canceling noise. This is because, as indicated by the equation (3), since the updating quantity for the filter coefficient W is calculated while ignoring the imaginary term Ie of the error signal e, when the canceling noise depending on the real term Re is radiated into the passenger compartment, it takes a long period of time until the noise in the passenger compartment including the noise depending on the imaginary term Ie is canceled out, and hence the noise in the passenger compartment cannot reliably be reduced in a short period of time for achieving the present embodiment.

Accordingly, the active noise control system 10 shown in FIG. 1 is unable to reliably reduce the noise in the passenger compartment within a short period of time. A reliable reduction of the noise in the passenger compartment within a short period of time is a task to be achieved by the active noise control system 10.

An active noise control system 30 according to an embodiment of the present invention will be described below with reference to FIGS. 3 through 9. Those parts of the active noise control system 30 which are identical to those of the active noise control system 10 that serves as a basis of the present invention are denoted by identical reference characters, and will not be described in detail below.

Figure 3:
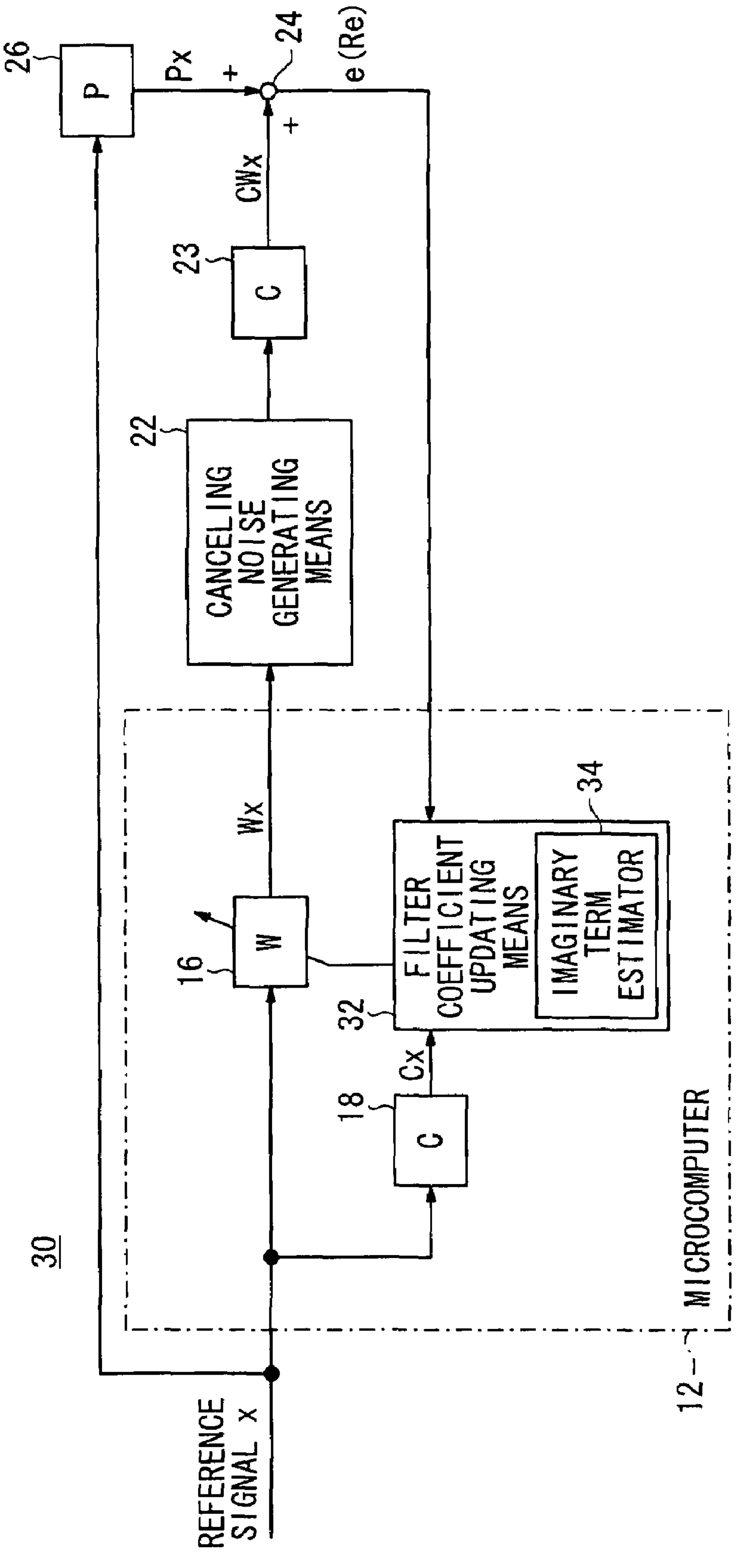
FIG. 3 is a block diagram of an active noise control system according to an embodiment of the present invention.

As shown in FIG. 3, the active noise control system 30 differs from the active noise control system 10 shown in FIG. 1 in that a filter coefficient updating means 32 has an imaginary term estimator 34 for estimating an imaginary term Ie based on the real term Re of the error signal e.

In the active noise control system 30, the imaginary term estimator 34 estimates an imaginary term Ie based on the real term Re of the error signal e, and the filter coefficient updating means 32 updates the filter coefficient W based on the real term Re, the imaginary term Ie, and the corrective signal C·x.

Specifically, in the active noise control system 30, the canceling noise generating means 22 outputs canceling noise in order to minimize the sum of $Re^2$ and $Ie^2$ as indicated by the following equation (22):

$$|e|^2=Re^2+Ie^2\rightarrow\text{minimum} \quad (22)$$

As a result, the LSM equations {corresponding to the equations (18) and (19) for the active noise control system 10 shown in FIG. 1} calculated by the filter coefficient updating means 32 are given as the following equations (23) and (24), and the equations {corresponding to the equations (20) and (21) for the active noise control system 10 shown in FIG. 1}for updating the filter coefficient W are given as the following equations (25) and (26):

$$\begin{aligned}\frac{\partial|e|^2}{\partial R_W} &= 2R_e\cdot\frac{\partial R_e}{\partial R_W}+2I_e\cdot\frac{\partial I_e}{\partial R_W}\\ &= 2R_e\cdot(R_CR_x-R_CI_x)+2I_e\cdot(R_CI_x-I_CR_x)\end{aligned} \quad (23)$$

$$\begin{aligned}\frac{\partial|e|^2}{\partial I_W} &= 2R_e\cdot\frac{\partial R_e}{\partial I_W}+2I_e\cdot\frac{\partial R_e}{\partial I_W}\\ &= 2R_e\cdot(-I_CR_x-R_CI_x)+2I_e\cdot(-I_CI_x-R_CR_x)\end{aligned} \quad (24)$$

$$Rw_{n+1}=Rwn-\mu\cdot\{\text{Re}\cdot(Rc\cdot Rx-Ic\cdot Ix)+Ie\cdot(Rc\cdot Ix+Ic\cdot Rx)\} \quad (25)$$

$$Iw_{n+1}=Iwn+\mu\cdot\{\text{Re}\cdot(Ic\cdot Rx+Rc\cdot Ix)+Ie\cdot(Ic\cdot Ix-Rc\cdot Rx)\} \quad (26)$$

Figure 4A:
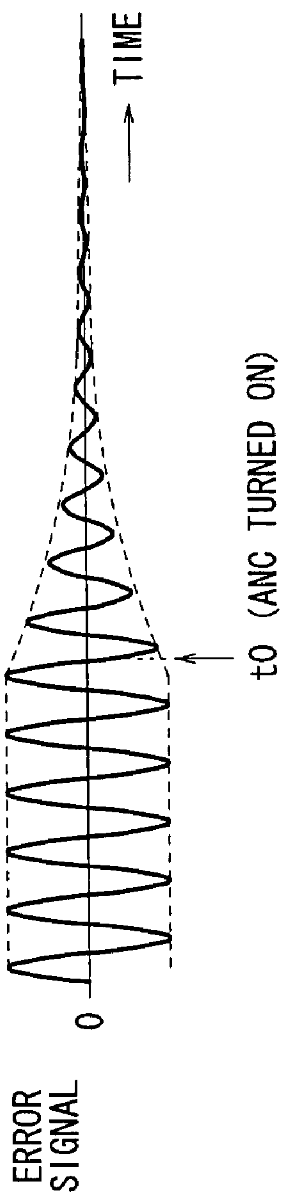
FIG. 4A is a diagram showing time-dependent changes of an error signal which occur when the active noise control system shown in FIG. 3 operates.
Figure 4B:
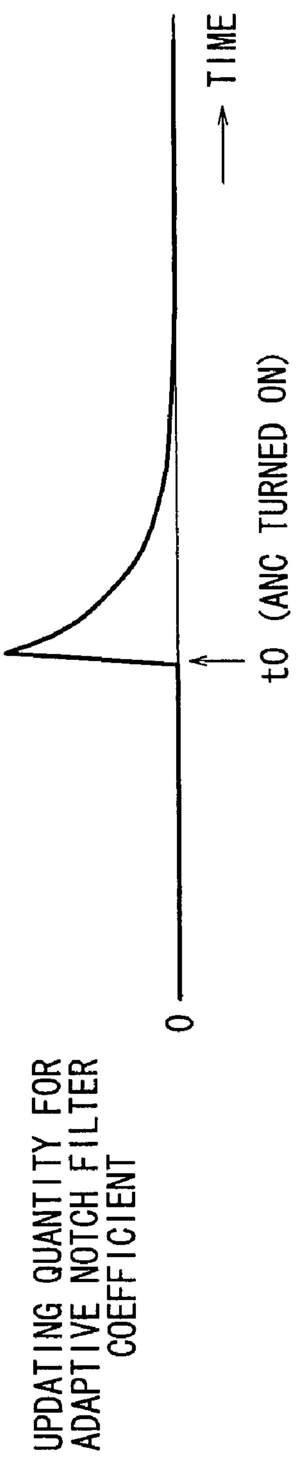
FIG. 4B is a diagram showing time-dependent changes of an updating quantity for a filter coefficient which occur when the active noise control system shown in FIG. 3 operates.

FIG. 4A shows time-dependent changes of the error signal e, and FIG. 4B shows time-dependent changes of the updating quantity {represented by the second term on the right side of each of the equations (25) and (26)} for the filter coefficient W. In FIGS. 4A and 4B, the active noise control system 30 changes from an off-state to an on-state at time t0, as with FIGS. 2A and 2B.

As indicated by the equations (25) and (26), since the updating quantity for the filter coefficient W includes the real term Re and the imaginary term Ie of the error signal e, the updating quantity for the filter coefficient W is proportional to the amplitude (the square root of the sum of the square of the real term Re and the square of the imaginary term Ie) on a complex plane of the error signal e. Therefore, in the active noise control system 30, the updating quantity for the filter coefficient W is larger (see FIG. 4B) at times when the amplitude on the complex plane of the error signal e is greater (see FIG. 4A), and is smaller at times when the amplitude on the complex plane of the error signal e is smaller. In FIGS. 2A and 4A, the broken-line curves represent the magnitude of the amplitude on the complex plane of the error signal e.

Accordingly, in the active noise control system 30, since the updating quantity for the filter coefficient W does not change in synchronism with the time-dependent change in the level of the error signal e (see FIG. 4B), the error signal e can be converged to a zero level i.e., a level where the noise in the passenger compartment is canceled out by the canceling noise, within a short period of time.

The estimation of the imaginary term Ie by the imaginary term estimator 34 in the case where the error signal e is a periodic signal, i.e., a signal having a certain frequency, will be described below.

If the error signal e has an amplitude Ae, a phase θe, and an angular frequency ω, then the error signal e, the real term Re, and the imaginary term Ie are expressed according to the following equations (27) through (29):

$$e=Ae\cdot e^{i(\omega t+\theta e)} \quad (27)$$

$$Re=Ae\cdot\cos(\omega t+\theta e) \quad (28)$$

$$Ie=Ae\cdot\sin(\omega t+\theta e) \quad (29)$$

The imaginary term estimator 34 estimates the imaginary term Ie by differentiating the real term Re with respect to time t, as indicated by the following equations (30) and (31):

$$\frac{\partial R_e}{\partial t} = -\omega A_e \sin(\omega t + \theta_e) = -\omega Ie \quad (30)$$

$$I_e = -\omega^{-1}\frac{\partial R_e}{\partial t} \quad (31)$$

Specifically, the imaginary term estimator 34 calculates a time differential value (∂Re/t) of the real term Re, and estimates (calculates) the imaginary term Ie by passing the calculated time differential value through a filter (first filter) having frequency response characteristics $-\omega^{-1}$. If the angular frequency ω is unknown, then the imaginary term estimator 34 may pass the time differential value through the filter having the above frequency response characteristics $-\omega^{-1}$. However, if the angular frequency ω is known, then the imaginary term estimator 34 may estimate (calculate) the imaginary term Ie by multiplying the time differential value by $-\omega^{-1}$ with the filter.

The error signal e can be expressed by a Fourier series according to the following equation (32):

$$e = \sum_{n=0}^{\infty} A_{e_n} e^{\omega_n t + \theta_{e_n}} \quad (32)$$

In this case, the imaginary term estimator 34 estimates the imaginary term Ie by passing the differential value of the real term Re at each frequency through the above filter (first filter) having the frequency response characteristics $-\omega^{-1}$.

The imaginary term estimator 34 may also estimate the imaginary term Ie by integrating the real term Re with respect to time according to the equation (33) shown below and passing the time integral value through a filter (first filter) having frequency response characteristics ω.

$$I_e = \omega \int R_e dt \quad (33)$$

If the angular frequency ω is unknown, then the imaginary term estimator 34 may pass the time integral value through the filter having the above frequency response characteristics ω. However, if the angular frequency ω is known, then the imaginary term estimator 34 may estimate (calculate) the imaginary term Ie by multiplying the time integral value by ω with the filter.

The calculation of a time differential value according to a differential method performed by the imaginary term estimator 34 and the calculation of the imaginary term Ie using the calculated time differential value will be described below.

The imaginary term estimator 34 determines the difference between the real term Re of the error signal e that is input in a present cycle and the real term Re of the error signal e that is input in a preceding cycle in each predetermined sampling period, and divides the difference by the sampling period to calculate the time differential value and the imaginary term Ie.

Sampling processes that are available include a fixed sampling period process for sampling data at a certain period (fixed period) and a variable sampling period process for sampling data at a frequency which is a multiple of a basic frequency, i.e. the frequency of a reference signal.

If the error signal e has a frequency fe and the sampling frequency (the reciprocal of the sampling period) is represented by fs, then the angular frequency ω is expressed according to the following equation (34), and the imaginary term Ie according to the fixed sampling period process is estimated according to the following equation (35):

$$\omega = 2\pi fe \quad (34)$$

$$I_e = -\omega^{-1}\frac{\partial R_e}{\partial t} = -\omega^{-1}\frac{R_{e_n} - R_{e_{n-1}}}{f_s^{-1}} = -(R_{e_n} - R_{e_{n-1}})\frac{f_s}{2\pi f_e} \quad (35)$$

According to the variable sampling period process, the ratio (multiplied value) between the frequency fe of the error signal e and the sampling frequency fs is expressed according to the following equation (36), and the imaginary term Ie is estimated according to the following equation (37):

$$fs = Afe \quad (36)$$

$$I_e = -\omega^{-1}\frac{R_{e_n} - R_{e_{n-1}}}{f_s^{-1}} = -(R_{e_n} - R_{e_{n-1}})\frac{f_s}{2\pi f_e} = -(R_{e_n} - R_{e_{n-1}})\frac{A}{2\pi} \quad (37)$$

where A/2π is a constant. The imaginary term Ie can be estimated by a single multiplication and a single addition.

The calculation of a time integral value according to a differential method performed by the imaginary term estimator 34 and the calculation of the imaginary term Ie using the calculated time integral value will be described below.

The imaginary term estimator 34 integrates the real term Re of the error signal e that is input in a present cycle and the real term Re of the error signal e that is input in a preceding cycle within the interval of a predetermined sampling period. The sampling frequency fs is set to a sufficiently large value compared with the frequency fe of the error signal e.

According to the fixed sampling period process, the imaginary term Ie is calculated according to the following equation (38), and according to the variable sampling period process, the imaginary term Ie is calculated according to the following equation (39):

$$I_e = \omega \int R_e dt = 2\pi f_e \frac{(R_{e_n} + R_{e_{n-1}})}{2}\frac{1}{f_s} = (R_{e_n} + R_{e_{n-1}})\frac{\pi f_e}{f_s} \quad (38)$$

$$I_e = 2\pi f_e \frac{(R_{e_n} + R_{e_{n-1}})}{2}\frac{1}{f_s} = (R_{e_n} + R_{e_{n-1}})\frac{\pi f_e}{A f_s} = (R_{e_n} + R_{e_{n-1}})\frac{\pi}{A} \quad (39)$$

Specific details of the filter coefficient updating means 32 including the imaginary term estimator 34 will be described below with reference to FIGS. 5 through 9.

Figure 5:
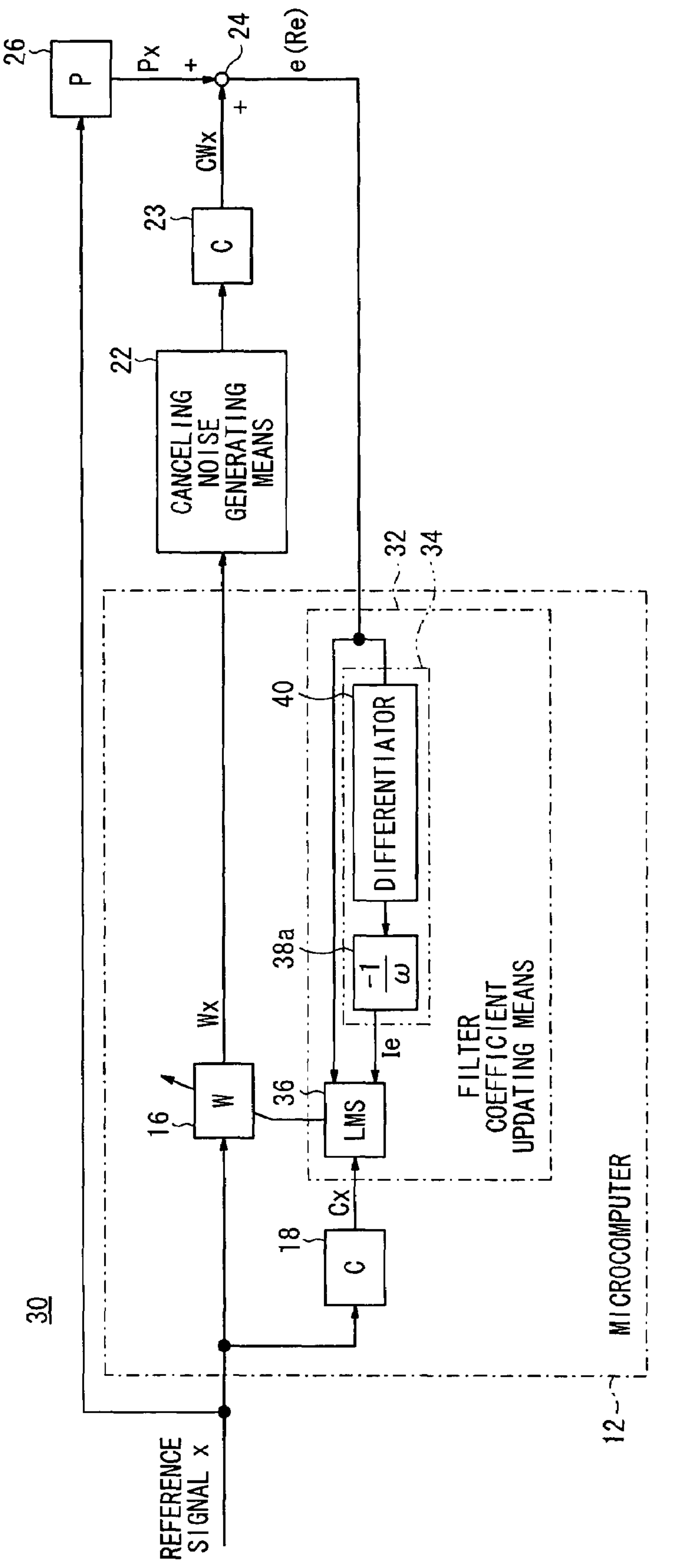
FIG. 5 is a block diagram of an imaginary term estimator shown in FIG. 3 which comprises a differentiator and a first filter.

FIG. 5 shows an imaginary term estimator 34 comprising a first filter 38*a* having characteristics $-\omega^{-1}$ and a differentiator (real term differentiator) 40. The imaginary term estimator 34 shown in FIG. 5 is capable of calculating the equations (31), (35), and (37). The filter coefficient updating means 32 also includes an LMS algorithm processor 36 for updating the filter coefficient W based on the imaginary term Ie from the imaginary term estimator 34, the real term Re of the error signal e from the microphone 24, and the corrective signal from the reference signal correcting means 18.

Figure 6:
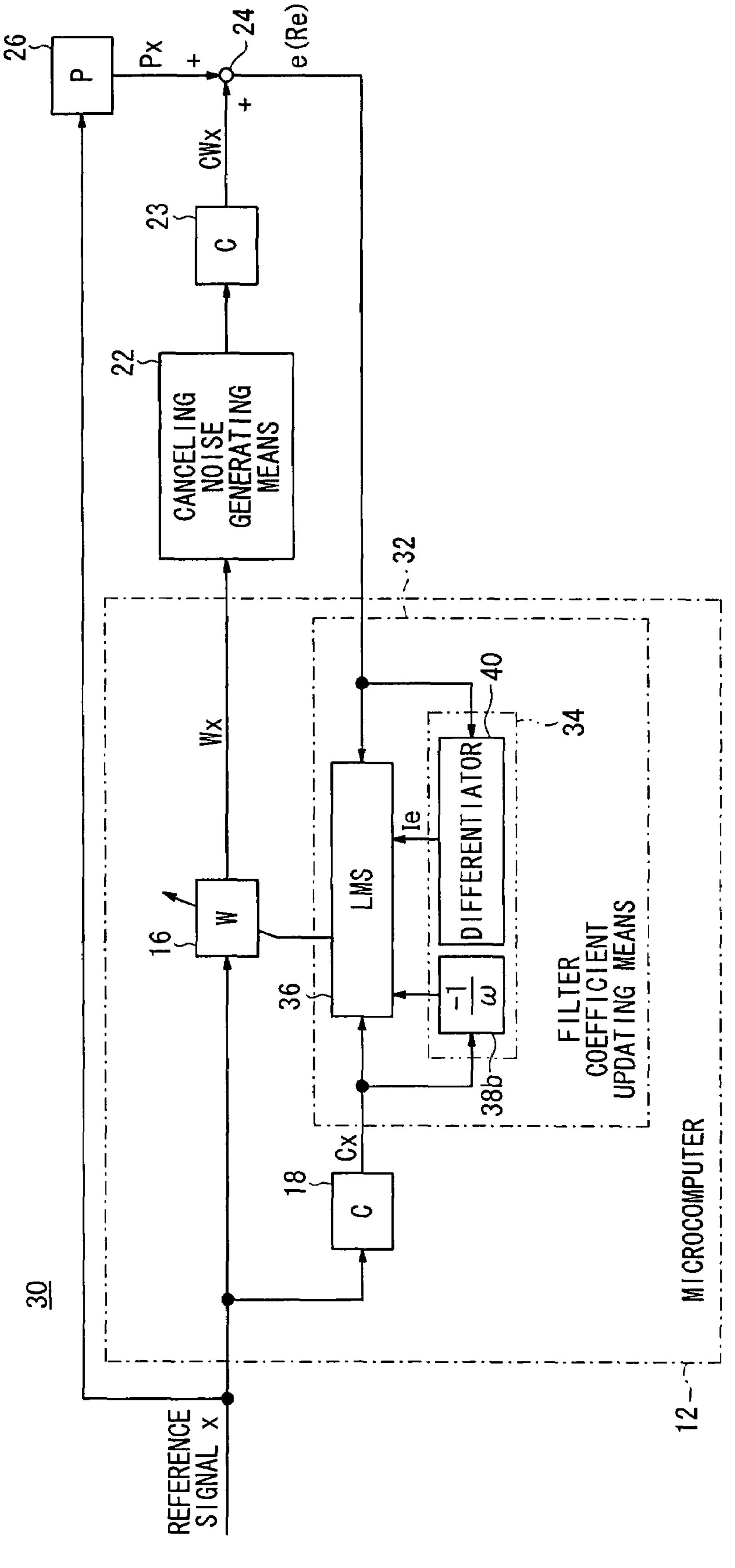
FIG. 6 is a block diagram of an imaginary term estimator shown in FIG. 3 which comprises a differentiator and a second filter.

FIG. 6 shows an imaginary term estimator 34 comprising a second filter 38*b* having characteristics $-\omega^{-1}$ and a differentiator 40. The second filter 38*b* passes the corrective signal from the reference signal correcting means 18 therethrough to the LMS algorithm processor 36, and the differentiator 40 outputs the time differential value of the real term Re to the LMS algorithm processor 36.

When the filter coefficient updating means 32 updates the filter coefficient W, the updating quantity {represented by the second term on the right side of each of the equations (20), (21), (25) and (26)} for the filter coefficient W includes the real term Re and the imaginary term Ie of the error signal e, the real term Rx and the imaginary term Ix of the reference signal x, and the real term Rc and the imaginary term Ic of the sound transfer characteristics C. In other words, the corrective signal which is represented by the product of the reference signal x and the sound transfer characteristics C is included in the updating quantity. Therefore, with respect to the updating quantity, dividing the error signal e by the angular frequency ω is synonymous with dividing the reference signal x by the angular frequency ω or dividing the corrective signal by the angular frequency ω. The signal generated by the second filter 38*b* when the corrective signal is multiplied by $-\omega^{-1}$ is essentially synonymous with a signal generated when the time differential value is multiplied by $-\omega^{-1}$.

Figure 7:
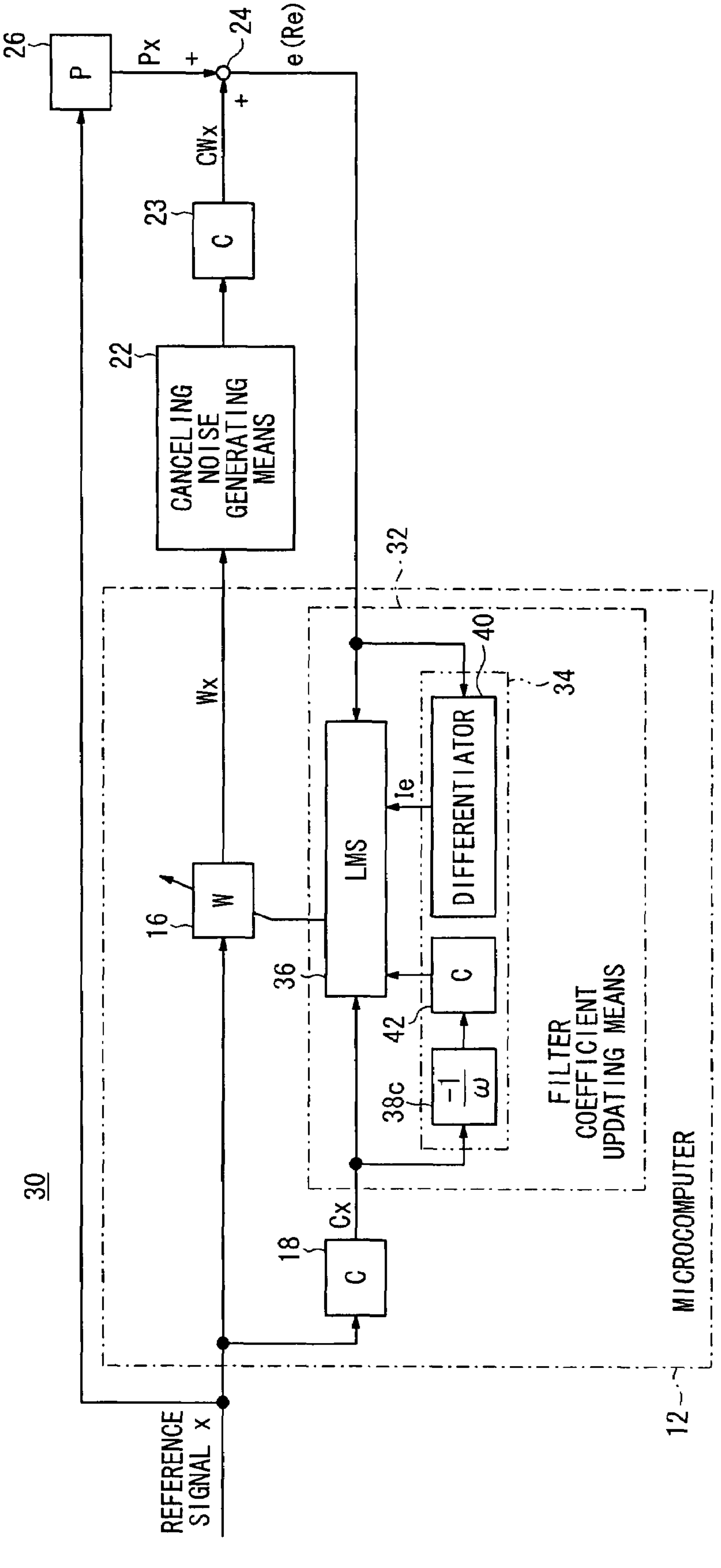
FIG. 7 is a block diagram of an imaginary term estimator shown in FIG. 3 which comprises a differentiator, a third filter, and a reference signal corrector.

FIG. 7 shows an imaginary term estimator 34 comprising a third filter 38*c* having characteristics $-\omega^{-1}$, a differentiator 40, and a reference signal corrector 42 having the sound transfer characteristics C. The third filter 38*c* passes the reference signal x therethrough and outputs a signal $-\omega^{-1}\cdot x$ to reference signal corrector 42. The reference signal corrector 42 multiplies the signal $-\omega^{-1}\cdot x$ by the sound transfer characteristics C and outputs a signal $-\omega^{-1}\cdot x\cdot C$ to the LMS algorithm processor 36. The differentiator 40 outputs a time differential value of the real term Re to the LMS algorithm processor 36. For the reasons described above, the signal output through the third filter 38*c* and the reference signal corrector 42 to LMS algorithm processor 36 is synonymous with a signal produced by multiplying the time differential value by $-\omega^{-1}$.

Figure 8:
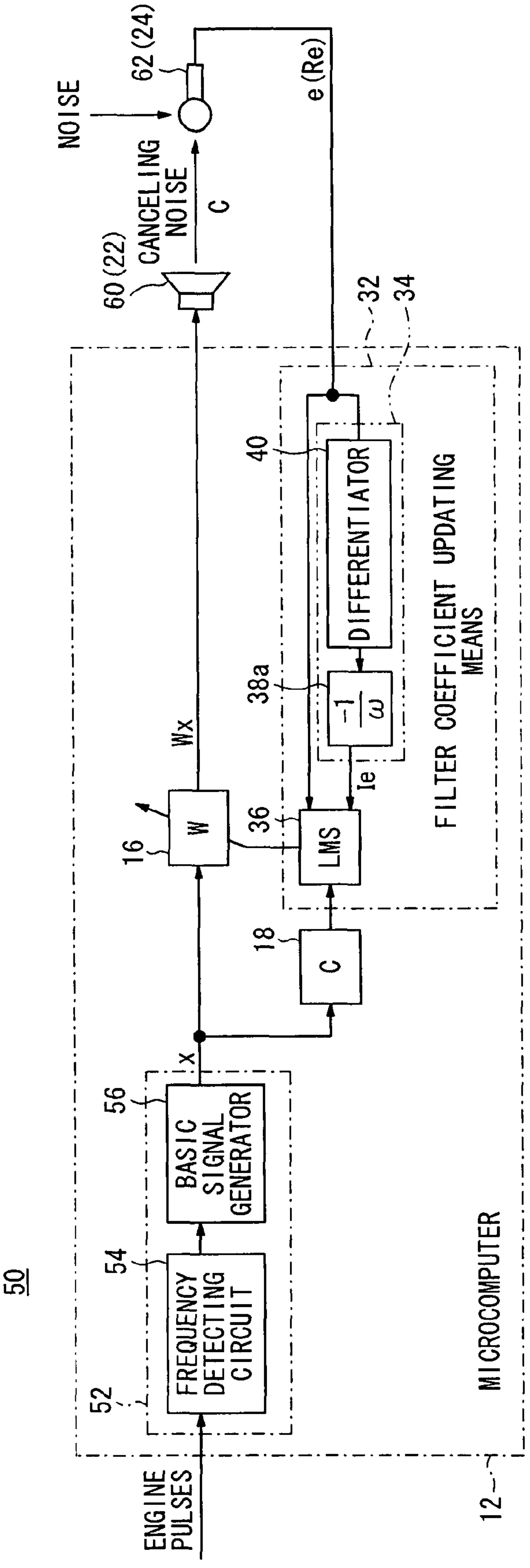
FIG. 8 is a block diagram of a modified active noise control system which is similar to the active noise control system shown in FIG. 5 except that it includes a reference signal generating means.

FIG. 8 shows in detailed block form a modified active noise control system which is similar to the active noise control system shown in FIG. 5. The active noise control system is different from the active noise control system shown in FIG. 5 in that the microcomputer 12 additionally has a reference signal generating means 52 having a frequency detecting circuit 54 and a basic signal generator 56 is connected to the input terminals of the adaptive filter 16 and the reference signal correcting means 18. In FIG. 8, the plant 26 shown in FIG. 5 is omitted, and noise applied to the microphone 62 is reduced by canceling noise radiated from a speaker 60.

The frequency detecting circuit 54 comprises a frequency counter for detecting the frequency of engine pulses (engine rotational frequency) each produced by a Hall device or the like per revolution of the output shaft of the non-illustrated engine on the vehicle, as representing a running state of the vehicle. The basic signal generator 56 generates a predetermined harmonic basic signal (reference signal) from a fundamental frequency which is the frequency detected by the frequency detecting means 54, and outputs the basic signal to the adaptive filter 16 and the reference signal correcting means 18.

Figure 9:
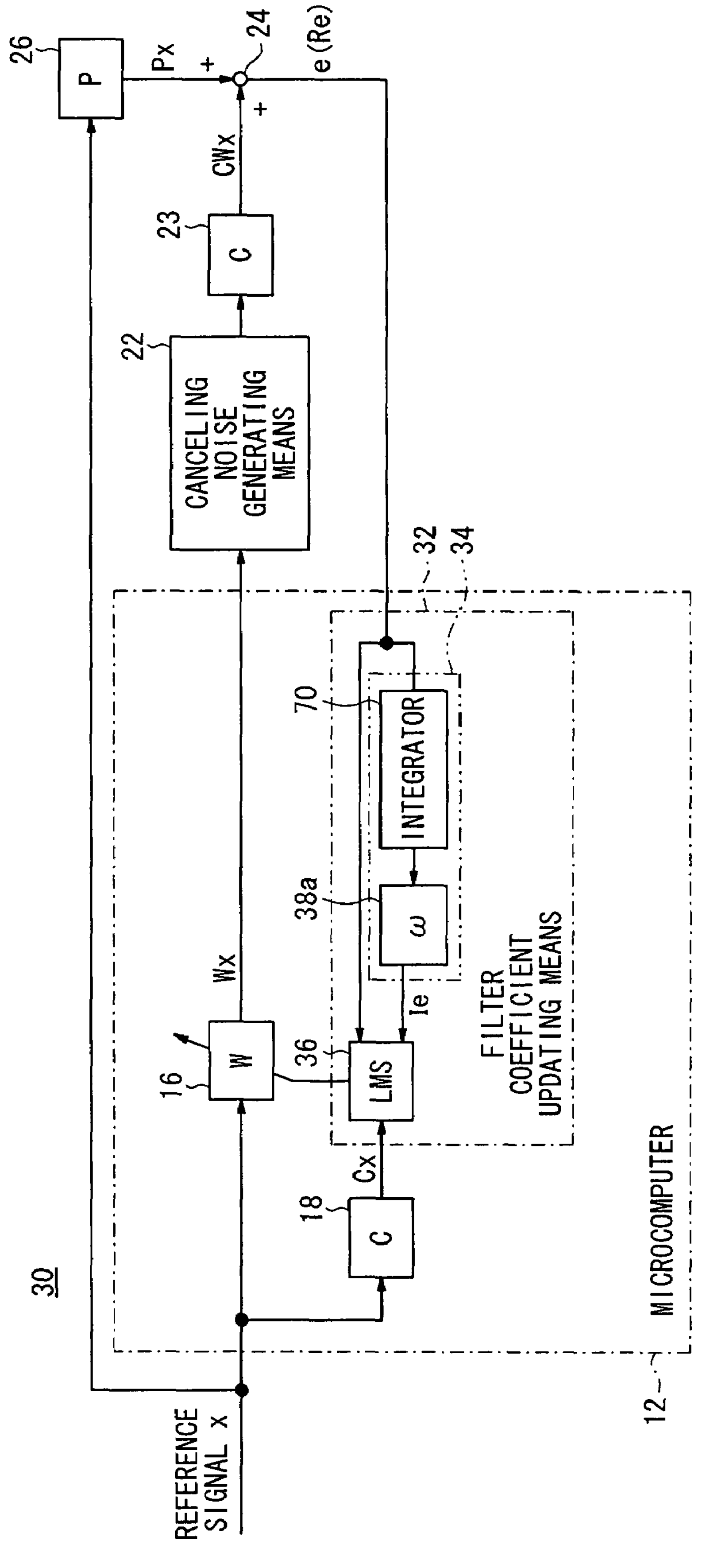
FIG. 9 is a block diagram of an imaginary term estimator shown in FIG. 3 which comprises an integrator and a first filter.

FIG. 9 shows an imaginary term estimator 34 comprising a first filter 38*a* having characteristics ω and an integrator (real term integrator) 70. The imaginary term estimator 34 shown in FIG. 9 is capable of calculating the equations (33), (38) and (39).

In the active noise control system 30, as described above, the imaginary term estimator 34 estimates the imaginary term Ie of the error signal e, and the filter coefficient updating means 32 updates the filter coefficient W based on the real term Re, the imaginary term Ie, and the corrective signal. Consequently, the updating quantity for the filter coefficient W is greater than that in the conventional system wherein the filter coefficient W is updated using only the real term Re and the corrective signal while ignoring the imaginary term Ie. As a result, the noise in the vicinity of the ears of the passengers in the passenger compartment can reliably be reduced within a short period of time.

The imaginary term estimator 34 may have the differentiator 40 for calculating a time differential value of the real term Re or the integrator 70 for calculating a time integral value of the real term Re. With such an arrangement, it is possible to estimate the imaginary term Ie based on a predetermined sampling period for efficiently reducing the noise in the passenger compartment.

The imaginary term estimator 34 also has the first filter 38*a* for dividing the time differential value calculated by the differentiator 40 by the angular frequency ω corresponding to the frequency fe of the error signal e and multiplying the time differential value by −1, or for multiplying the time integral value calculated by the integrator 70 by the angular frequency ω. If the error signal e is a periodic signal and the frequency fe of the error signal e is known, then the component of the angular frequency ω (the frequency characteristics ω) generated when the time differential value or the time integral value is calculated can be canceled. Therefore, the imaginary term Ie can be estimated with accuracy.

If the error signal e is a periodic signal and the frequency fe of the error signal e is unknown, then the time differential value or the time integral value is passed through the first filter 38*a* having the characteristics $-\omega^{-1}$ or ω, thereby canceling the component of the angular frequency ω (the frequency characteristics ω generated when the time differential value or the time integral value is calculated. Therefore, the imaginary term Ie can also be estimated with accuracy.

If the imaginary term estimator 34 has the second filter 38*b* for dividing the corrective signal by the angular frequency ω corresponding to the frequency fe of the error signal e, then since the updating quantity for the filter coefficient W includes the error signal e, the reference signal x, and the corrective signal, dividing the corrective signal by the angular frequency ω is preferable as it is synonymous with dividing the time differential value by the angular frequency ω. The second filter 38*b* which has the characteristics $-\omega^{-1}$ is also capable of performing the same function.

The imaginary term estimator 34 should also preferably have the third filter 38*c* for dividing the reference signal x by the angular frequency ω corresponding to the frequency fe of the error signal e, and the reference signal corrector 42 for correcting the divided reference signal x based on the sound transfer characteristics C. For the reasons described above, dividing the reference signal x by the angular frequency ω is preferable as it is synonymous with dividing the time differential value by the angular frequency ω. The third filter 38*c* which has the characteristics $-\omega^{-1}$ is also capable of performing the same function.

If the control signal and the corrective signal are generated, the canceling noise is output, the error signal e is detected, and the filter coefficient W is updated successively in each given sampling period, then the differentiator 40 may calculate the time differential value by dividing, by the sampling period, the difference between the real term Re of the error signal e that is input in a present sampling cycle and the real term Re of the error signal e that is input in a preceding sampling cycle. In this manner, the imaginary term Ie can easily be calculated.

If the sampling period is a fixed sampling period, then the imaginary term estimator 34 may estimate the imaginary term Ie by dividing the difference by the fixed sampling period and the frequency fe of the error signal e and multiplying the difference by −1. If the sampling period is a variable sampling period, then the imaginary term estimator 34 may estimate the imaginary term Ie by multiplying the difference by a number A which represents the reciprocal of the product of the variable sampling period and the frequency fe of the error signal e, and also by −1. In this manner, it is possible to estimate the imaginary term Ie regardless of the fixed sampling period process or the variable sampling period process.

If the error signal e is a periodic signal and the frequency fe of the error signal e is unknown, then it is possible to estimate the imaginary term Ie regardless of the fixed sampling period process or the variable sampling period process, by giving the first filter 38*a* the characteristics $-\omega^{-1}$.

If the control signal and the corrective signal are generated, the canceling noise is output, the error signal e is detected, and the filter coefficient W is updated successively in each given sampling period, then the integrator 70 may calculate the time integral value by multiplying, by the sampling period, the sum of the real term Re of the error signal e that is input in a present sampling cycle and the real term Re of the error signal e that is input in a preceding sampling cycle. In this manner, the imaginary term Ie can easily be calculated.

If the sampling period is a fixed sampling period, then the imaginary term estimator 34 may estimate the imaginary term Ie by multiplying the sum by the fixed sampling period and the frequency fe of the error signal e. If the sampling period is a variable sampling period, then the imaginary term estimator 34 may estimate the imaginary term Ie by dividing the sum by a number A which represents the reciprocal of the product of the variable sampling period and the frequency fe of the error signal e. In this manner, it is possible to estimate the imaginary term Ie regardless of the fixed sampling period process or the variable sampling period process.

If the error signal e is a periodic signal and the frequency fe of the error signal e is unknown, then it is possible to estimate the imaginary term Ie regardless of the fixed sampling period process or the variable sampling period process, by giving the first filter 38*a* the characteristics ω.

According to the above embodiment, the active noise control systems 10, 30, 50 have been described. The principles of the present invention are also applicable to an active vibration control system 80 shown in FIG. 10. In the active vibration control system 80, a signal which is correlated to first vibration generated from a vibration source such as an engine on a vehicle or the like is input as a reference signal x to the adaptive filter 16 and the reference signal correcting means 18. The canceling noise generating means 22 in the preceding embodiment is replaced with a vibration output means 82 such as an actuator or the like for vibrating a vibration producing object such as a vehicle body or the like based on the control signal from the adaptive filter 16, and the microphone 24 in the preceding embodiment is replaced with a vibration detecting means 84 such as an acceleration sensor or the like.

Figure 10:
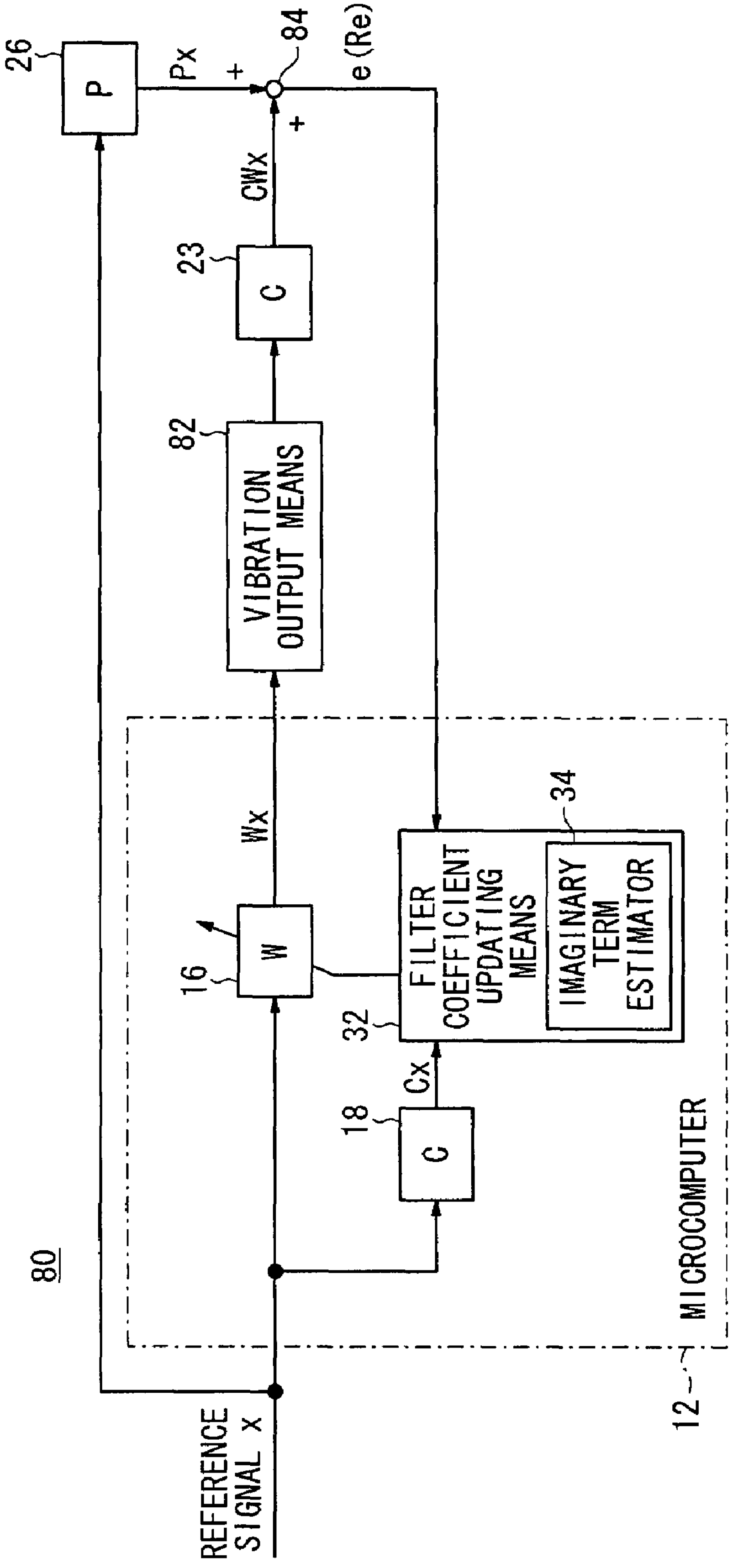
FIG. 10 is a block diagram of an active vibration control system according to an embodiment of the present invention.

In FIG. 10, P×x represents vibration (second vibration) produced in the vehicle by the first vibration, C represents vibration transfer characteristics in the transmission path 23 from the vibration output means 82 to the vibration detecting means 84, and C×W×x vibration (third vibration) applied to the vibration producing object for canceling out the second vibration. The vibration detecting means 84 detects canceling error vibration between the second vibration P×x and the third vibration C×W×x, and outputs an error signal e based on the canceling error vibration to the filter coefficient updating means 32.

With the above arrangement, the imaginary term estimator 34 estimates the imaginary term Ie of the error signal e from the vibration detecting means 84, and the filter coefficient updating means 32 updates the filter coefficient W based on the imaginary term Ie, the real term Re, and the corrective signal (=C×x). Therefore, the updating quantity for the filter coefficient W is increased, and the vibration in the vehicle can reliably be reduced in a short period of time.

Although certain preferred embodiments of the present invention have been shown and described in detail, it should be understood that various changes and modifications may be made therein without departing from the scope of the appended claims.

What is claimed is:

1. An active noise control system comprising:

an adaptive filter for being supplied with a reference signal that is correlated to first noise generated by a noise source on a vehicle, and generating a control signal based on the reference signal;

noise output means for outputting third noise based on said control signal in order to cancel out second noise generated in the vehicle based on said first noise;

noise detecting means for generating an error signal based on canceling error noise between said second noise and said third noise;

reference signal correcting means for correcting said reference signal based on sound transfer characteristics from said noise output means to said noise detecting means, and outputting the corrected reference signal as a corrective signal; and filter coefficient updating means, having an imaginary term estimator for estimating an imaginary term of said error signal based on the error signal which comprises a real term, for updating a filter coefficient of said adaptive filter in order to minimize said error signal, based on said imaginary term estimated by said imaginary term estimator, said real term, and said corrective signal, wherein said imaginary term estimator has a real term differentiator for calculating a time differential value of said real term, and estimates said imaginary term based on the time differential value calculated by said real term differentiator.

2. An active noise control system according to claim 1, wherein said imaginary term estimator further has a first filter for dividing the time differential value calculated by said real term differentiator by an angular frequency corresponding to the frequency of said error signal and multiplying the time differential value by −1.

3. An active noise control system according to claim 1, wherein said imaginary term estimator further has a first filter having characteristics represented by the reciprocal, multiplied by −1, of an angular frequency corresponding to the frequency of said error signal, for passing therethrough said time differential value calculated by said real term differentiator.

4. An active noise control system according to claim 1, wherein when said control signal and said corrective signal are generated, said third noise is output, said error signal is detected, and said filter coefficient is updated successively in each given sampling period, said real term differentiator calculates said time differential value by dividing, by said sampling period, the difference between the real term of the error signal that is input in a present sampling cycle and the real term of the error signal that is input in a preceding sampling cycle.

5. An active noise control system according to claim 4, wherein if said sampling period is a fixed sampling period, said imaginary term estimator estimates said imaginary term by dividing said difference by said fixed sampling period and the frequency of said error signal and multiplying said difference by −1.

6. An active noise control system according to claim 4, wherein if said sampling period is a fixed sampling period, said imaginary term estimator estimates said imaginary term by dividing said difference by said fixed sampling period and passing the divided difference through a first filter having characteristics represented by the reciprocal, multiplied by −1, of an angular frequency corresponding to the frequency of said error signal.

7. An active noise control system according to claim 4, wherein if said sampling period is a variable sampling period, said imaginary term estimator estimates said imaginary term by multiplying said difference by a number representing the reciprocal of the product of said variable sampling period and the frequency of said error signal and by −1.

8. An active noise control system according to claim 4, wherein if said sampling period is a variable sampling period, said imaginary term estimator estimates said imaginary term by dividing said difference by said variable sampling period and passing the divided difference through a first filter having characteristics represented by the reciprocal, multiplied by −1, of an angular frequency corresponding to the frequency of said error signal.

9. An active noise control system according to claim 1, wherein said noise source comprises an engine on said vehicle;

said second noise comprises noise produced in a passenger compartment of said vehicle;

said noise output means comprises a speaker disposed in said passenger compartment; and said noise detecting means comprises a microphone disposed in said passenger compartment.

10. An active noise control system comprising:

an adaptive filter for being supplied with a reference signal that is correlated to first noise generated by a noise source on a vehicle, and generating a control signal based on the reference signal;

noise output means for outputting third noise based on said control signal in order to cancel out second noise generated in the vehicle based on said first noise;

noise detecting means for generating an error signal based on canceling error noise between said second noise and said third noise;

reference signal correcting means for correcting said reference signal based on sound transfer characteristics from said noise output means to said noise detecting means, and outputting the corrected reference signal as a corrective signal; and filter coefficient updating means, having an imaginary term estimator for estimating an imaginary term of said error signal based on the error signal which comprises a real term, for updating a filter coefficient of said adaptive filter in order to minimize said error signal, based on said imaginary term estimated by said imaginary term estimator, said real term, and said corrective signal, wherein said imaginary term estimator has a real term integrator for calculating a time integral value of said real term, and estimates said imaginary term based on the time integral value calculated by said real term integrator.

11. An active noise control system according to claim 10, wherein said imaginary term estimator further has a first filter for multiplying the time integral value calculated by said real term integrator by an angular frequency corresponding to the frequency of said error signal.

12. An active noise control system according to claim 10, wherein said imaginary term estimator further has a first filter having characteristics represented by an angular frequency corresponding to the frequency of said error signal, for passing therethrough the time integral value calculated by said real term integrator.

13. An active noise control system according to claim 10, wherein when said control signal and said corrective signal are generated, said third noise is output, said error signal is detected, and said filter coefficient is updated successively in each given sampling period, said real term integrator calculates said time integral value by multiplying, by said sampling period, the sum of the real term of the error signal that is input in a present sampling cycle and the real term of the error signal that is input in a preceding sampling cycle.

14. An active noise control system according to claim 13, wherein if said sampling period is a fixed sampling period, said imaginary term estimator estimates said imaginary term by multiplying said sum by said fixed sampling period and the frequency of said error signal.

15. An active noise control system according to claim 13, wherein if said sampling period is a fixed sampling period, said imaginary term estimator estimates said imaginary term by multiplying said sum by said fixed sampling period and passing the multiplied sum through a first filter having characteristics represented by an angular frequency corresponding to the frequency of said error signal.

16. An active noise control system according to claim 13, wherein if said sampling period is a variable sampling period, said imaginary term estimator estimates said imaginary term by dividing said sum by a number representing the reciprocal of the product of said variable sampling period and the frequency of said error signal.

17. An active noise control system according to claim 13, wherein if said sampling period is a variable sampling period, said imaginary term estimator estimates said imaginary term by multiplying said sum by said variable sampling period and passing the multiplied sum through a first filter having characteristics represented by an angular frequency corresponding to the frequency of said error signal.

18. An active noise control system comprising:

an adaptive filter for being supplied with a reference signal that is correlated to first noise generated by a noise source on a vehicle, and generating a control signal based on the reference signal;

noise output means for outputting third noise based on said control signal in order to cancel out second noise generated in the vehicle based on said first noise, noise detecting means for generating an error signal based on canceling error noise between said second noise and said third noise;

reference signal correcting means for correcting said reference signal based on sound transfer characteristics from said noise output means to said noise detecting means, and outputting the corrected reference signal as a corrective signal; and filter coefficient updating means, having an imaginary term estimator for estimating an imaginary term of said error signal based on the error signal which comprises a real term, for updating a filter coefficient of said adaptive filter in order to minimize said error signal, based on said imaginary term estimated by said imaginary term estimator, said real term, and said corrective signal, wherein said imaginary term estimator has a second filter for dividing said corrective signal by an angular frequency corresponding to the frequency of said error signal and multiplying said corrective signal by −1.

19. An active noise control system comprising:

an adaptive filter for being supplied with a reference signal that is correlated to first noise generated by a noise source on a vehicle, and generating a control signal based on the reference signal;

noise output means for outputting third noise based on said control signal in order to cancel out second noise generated in the vehicle based on said first noise;

noise detecting means for generating an error signal based on canceling error noise between said second noise and said third noise;

reference signal correcting means for correcting said reference signal based on sound transfer characteristics from said noise output means to said noise detecting means, and outputting the corrected reference signal as a corrective signal; and filter coefficient updating means, having an imaginary term estimator for estimating an imaginary term of said error signal based on the error signal which comprises a real term, for updating a filter coefficient of said adaptive filter in order to minimize said error signal, based on said imaginary term estimated by said imaginary term estimator, said real term, and said corrective signal, wherein said imaginary term estimator has a second filter having characteristics represented by the reciprocal, multiplied by −1, of an angular frequency corresponding to the frequency of said error signal, for passing said corrective signal therethrough.

20. An active noise control system comprising:

an adaptive filter for being supplied with a reference signal that is correlated to first noise generated by a noise source on a vehicle, and generating a control signal based on the reference signal;

noise output means for outputting third noise based on said control signal in order to cancel out second noise generated in the vehicle based on said first noise;

noise detecting means for generating an error signal based on canceling error noise between said second noise and said third noise;

reference signal correcting means for correcting said reference signal based on sound transfer characteristics from said noise output means to said noise detecting means, and outputting the corrected reference signal as a corrective signal; and filter coefficient updating means, having an imaginary term estimator for estimating an imaginary term of said error signal based on the error signal which comprises a real term, for updating a filter coefficient of said adaptive filter in order to minimize said error signal, based on said imaginary term estimated by said imaginary term estimator, said real term, and said corrective signal, wherein said imaginary term estimator has a third filter for dividing said reference signal by an angular frequency corresponding to the frequency of said error signal and multiplying said reference signal by −1, and a reference signal corrector for correcting the divided and multiplied reference signal based on said sound transfer characteristics.

21. An active noise control system comprising:

an adaptive filter for being supplied with a reference signal that is correlated to first noise generated by a noise source on a vehicle, and generating a control signal based on the reference signal;

noise output means for outputting third noise based on said control signal in order to cancel out second noise generated in the vehicle based on said first noise;

noise detecting means for generating an error signal based on canceling error noise between said second noise and said third noise;

reference signal correcting means for correcting said reference signal based on sound transfer characteristics from said noise output means to said noise detecting means, and outputting the corrected reference signal as a corrective signal; and filter coefficient updating means, having an imaginary term estimator for estimating an imaginary term of said error signal based on the error signal which comprises a real term, for updating a filter coefficient of said adaptive filter in order to minimize said error signal, based on said imaginary term estimated by said imaginary term estimator, said real term, and said corrective signal, wherein said imaginary term estimator has a third filter having characteristics represented by the reciprocal, multiplied by −1, of an angular frequency corresponding to the frequency of said error signal, for passing said corrective signal therethrough, and a reference signal corrector for correcting the reference signal having passed through said third filter based on said sound transfer characteristics.

* * * * *